(12) United States Patent
Tsumatori (10) Patent No.: US 10,456,040 B2
(45) Date of Patent: Oct. 29, 2019

(54) IMAGING DEVICE

(71) Applicant: SHIMADZU CORPORATION, Nakagyo-Ku, Kyoto-Shi, Kyoto (JP)

(72) Inventor: Hiroyuki Tsumatori, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 267 days.

(21) Appl. No.: 15/511,550

(22) PCT Filed: Jul. 8, 2015

(86) PCT No.: PCT/JP2015/069606
§ 371 (c)(1),
(2) Date: Mar. 15, 2017

(87) PCT Pub. No.: WO2016/042892
PCT Pub. Date: Mar. 24, 2016

(65) Prior Publication Data
US 2017/0258330 A1    Sep. 14, 2017

(30) Foreign Application Priority Data

Sep. 18, 2014 (JP) .................................. 2014-189627

(51) Int. Cl.
*A61B 5/00* (2006.01)

(52) U.S. Cl.
CPC .......... *A61B 5/0035* (2013.01); *A61B 5/0071* (2013.01); *A61B 5/0077* (2013.01); *A61B 2562/0233* (2013.01); *A61B 2576/00* (2013.01)

(58) Field of Classification Search
CPC ... A61B 5/0035; A61B 5/0071; A61B 5/0077; A61B 5/7425; A61B 2562/0233; A61B 2576/00; G01N 21/6456; G06T 5/50; G06T 2207/10048; G06T 2207/10064; G06T 2207/20221
USPC ........................................................ 600/431
See application file for complete search history.

(56) References Cited

U.S. PATENT DOCUMENTS

2012/0268573 A1* 10/2012 Schonborn ............. A61B 1/051
348/49

FOREIGN PATENT DOCUMENTS

| JP | 10-201707 | 8/1998 |
| JP | 2002-65602 | 3/2002 |
| JP | 2009-226072 | 10/2009 |
| WO | WO2009/139466 | 11/2009 |

(Continued)

OTHER PUBLICATIONS

PCT/JP2015/069606, ISR dated Oct. 6, 2015, 1 page—English, 2 pages—Japanese3; Written Opinion—2 page—English with certificate of translation, 5 pages—Japanese.

(Continued)

*Primary Examiner* — Amanda K Hulbert
(74) *Attorney, Agent, or Firm* — Andrew F. Young, Esq.; Lackenbach Siegel, LLP (57) ABSTRACT

The fusion element of the imaging processing element 31 generates the fused image by combining: the corrected image generated by using; at least one parameter relative to the color space including RGB value of each pixel, luminance, value, saturation and hue of the visible image, and each pixel value of the near-infrared image imaging fluorescences from indocyanine green; and the second corrected image that is the near-infrared image after colored.

4 Claims, 5 Drawing Sheets

(56) References Cited

FOREIGN PATENT DOCUMENTS

WO    WO 2012/164991    12/2012

OTHER PUBLICATIONS

JP 2016-548602, Argument dated Dec. 29, 2018, 3 pages—Japanese, 2 pages—English.
JP 2016-548602, Amendment dated Dec. 18, 2017, 2 pages—Japanese, 3 pages—English.
JP 2016-548602, Notice of Allowance dated Feb. 28, 2018, 2 pages—Japanese, 1 page—English.
JP 2016-548602, Reason for Refusal dated Oct. 6, 2017, 3 pages—Japanese, 2 pages—English.

* cited by examiner

IMAGING DEVICE

CROSS REFERENCE TO RELATED APPLICATIONS

This application relates to and claims § 371 priority from SN PCT/JP2015/069606 filed Jul. 8, 2015, the entire contents of which are incorporated herein by reference, which in turn claims priority to JP Ser. No. 2014-189627 filed Sep. 18, 2014.

FIGURE FOR PUBLICATION

FIG. 4

BACKGROUND OF THE INVENTION

Field of the Invention

The present invention relates to an imaging device that irradiates excitation light to the fluorescent dye (fluorophore) injected into the subject and images fluorescences emitted from the fluorophore therein.

Background

Recently, the method called near-infrared fluorescence imaging is applied in a surgery. According to the near-infrared fluorescence imaging, indocyanine green (ICG) as the fluorophore is injected into an affected area. And when near-infrared light as an excitation light having wavelength approximately 600-850 nm is irradiated to indocyanine green, indocyanine green emits fluorescence in the near-infrared region in which the peak of the wavelength is approximately 810 nm. Such fluorescence is imaged by a camera that can detect the near-infrared light, and then the image thereof is displayed on a display such as a liquid crystal display panel and so forth. According to such near-infrared fluorescence imaging, blood vessels and lymphatic vessels and so forth, which are around 20 mm below the body surface, can be observed.

Patent Document 1 discloses a data collection method for collecting the data of the area undetectable in the affected cancer area distribution image as the sub-affected cancer area data despite detectable in the strength-distribution image using the near-infrared fluorescence by comparing the near-infrared fluorescence strength-distribution image obtained by irradiating the excitation light for indocyanine green to the body's target organ in which indocyanine green is injected, and the cancer affected area distribution image obtained by applying an X-ray, a nuclear magnetic resonance or an ultrasound wave relative to the target organ before injecting indocyanine green.

In addition, Patent Document 2 discloses a surgery assist method using irradiating an excitation light and visible light alternately to the subject to which an angiographic contrast agent is administered, obtaining a fluorescent image and a visible image alternately to which the excitation lights are irradiated by an imaging means, extracting the blood vessel image by conducting a threshold processing relative to the fluorescent image using a predetermined threshold value and generating a fused image by superimposing the visible image and the extracted blood vessels image.

RELATED PRIOR ART DOCUMENTS

Patent Document

Patent Document 1: PCT International Publication No. WO2009-139466
Patent Document 2: JP Patent Published 2009-226072

ASPECTS AND SUMMARY OF THE INVENTION

Problems to be Solved by the Invention

According to Patent Document 2, when the fused image is generated by combining the visible image and the fluorescent image, after coloring the black and white fluorescent image, the visible image and the colored fluorescent image are combined by e.g., using the method for an additive fusion and the screen fusion and so forth. In such case, it is problematic that when the visible image and the fluorescent image after colored are simply fused, discrimination between the visible image and the colored fluorescent image may become difficult.

Specifically, when simply fused, the base color of the visible image and the color of the colored fluorescent image are mixed up and the fluorescent image is too far away from the inherent color thereof, so that it may be difficult to discriminate the limit of the fluorescence area of the fluorescent image.

The present invention is to provide solutions for the above set forth problems and provides an imaging device capable of improving visibility of the fluorescent image when the visible image and the fluorescent image of the subject are combined to generate a fused image.

Means for Solving the Problem

According to the first invention, an imaging device comprises: an excitation light source that irradiates the excitation light to a subject, wherein the excitation light excites a fluorophore administered into the subject; a visible light source that irradiates visible light to the subject; a camera capable of detecting the fluorescence and the visible light, wherein the fluorescence that is emitted from the fluorophore due to the irradiation of the excitation light, and the visible light that is reflected from the subject's surface are imaged; an image fusion element that generates the fused image by combining the visible image of the subject and the fluorescent image of the subject imaged by the camera; and wherein the image fusion element that generates the fused image by combining a first corrected image obtained by calculating using the visible image and the fluorescent image and a second corrected image by coloring the fluorescent image.

According to aspect of the second invention, the image fusion element that generates the fused image by combining the first corrected image obtained by subtracting an image based on the fluorescent image from the visible image and the second corrected image by coloring the fluorescent image obtained by coloring the fluorescent image.

According to aspect of the third invention, wherein the first corrected image is generated by subtracting the pixel value, which is obtained by multiplying a pixel value of the fluorescent image by a coefficient, which is larger than 0 and smaller than 1, from the value of the color space of the visible image.

According to aspect of the fourth invention, the excitation light and the fluorescence are the near-infrared light.

Effect of the Invention

According to the inventions as claimed, when a fused image is generated by combining the visible image and the fluorescent image of the subject, visibility of the fluorescent image can be improved based on combining the first corrected image obtained by calculating using the visible image and the fluorescent image and the second corrected image obtained by coloring the fluorescent image.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the imaging apparatus and devices and the elements herein, without limitation, and including the sub-components such as operational structures, circuits, PC boards, communication pathways, and related elements, control elements of all kinds in a physical sense however described, display circuits and display systems and elements, any necessary driving elements, inputs, sensors, detectors, electronic memory elements, processors and any combinations of these structures etc. as will be understood by those of skill in the art as also being identified as or capable of operating the systems and devices and subcomponents noted herein and structures that accomplish the functions noted herein without restrictive language or label requirements since those of skill in the art are well versed in related imaging device technology, computer and operational controls and technologies of radiographic devices and all their sub components, including various circuits and combinations of circuits without departing from the scope and spirit of the present invention.

Figure 1:
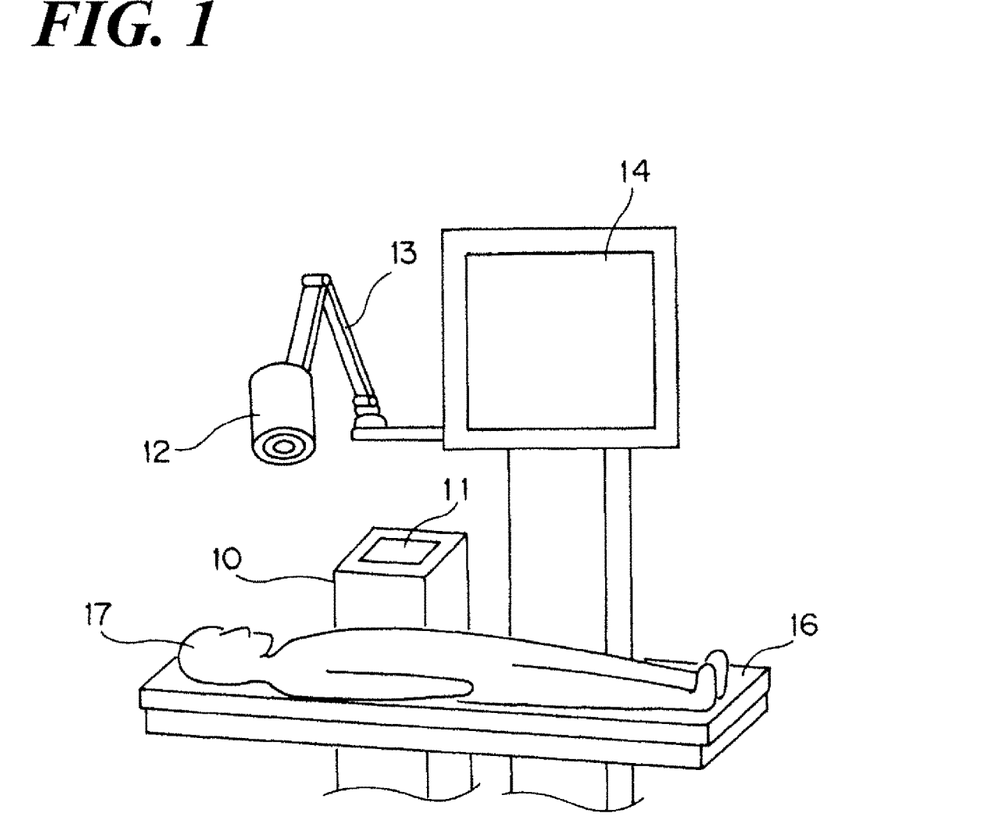
FIG. 1 is a schematic view of an imaging device according to the present invention.

The inventor sets forth Embodiments of the present invention based on the following FIGS. FIG. 1 is a schematic view of an imaging device according to the present invention.

The imaging device of the present invention further comprises: an input element 11 such as a touch panel and so forth; a main body 10 including a control element 30 inside, set forth later; a lighting-imaging element 12 movably supported by an arm 13; a display element 14 including such as a liquid crystal display panel; and a treatment table 16 on which a subject (patient) 17 would be loaded. In addition, the lighting-imaging element 12 is not limited to be supported by the arm 13, but may be carried in an operator's hands.

Figure 2:
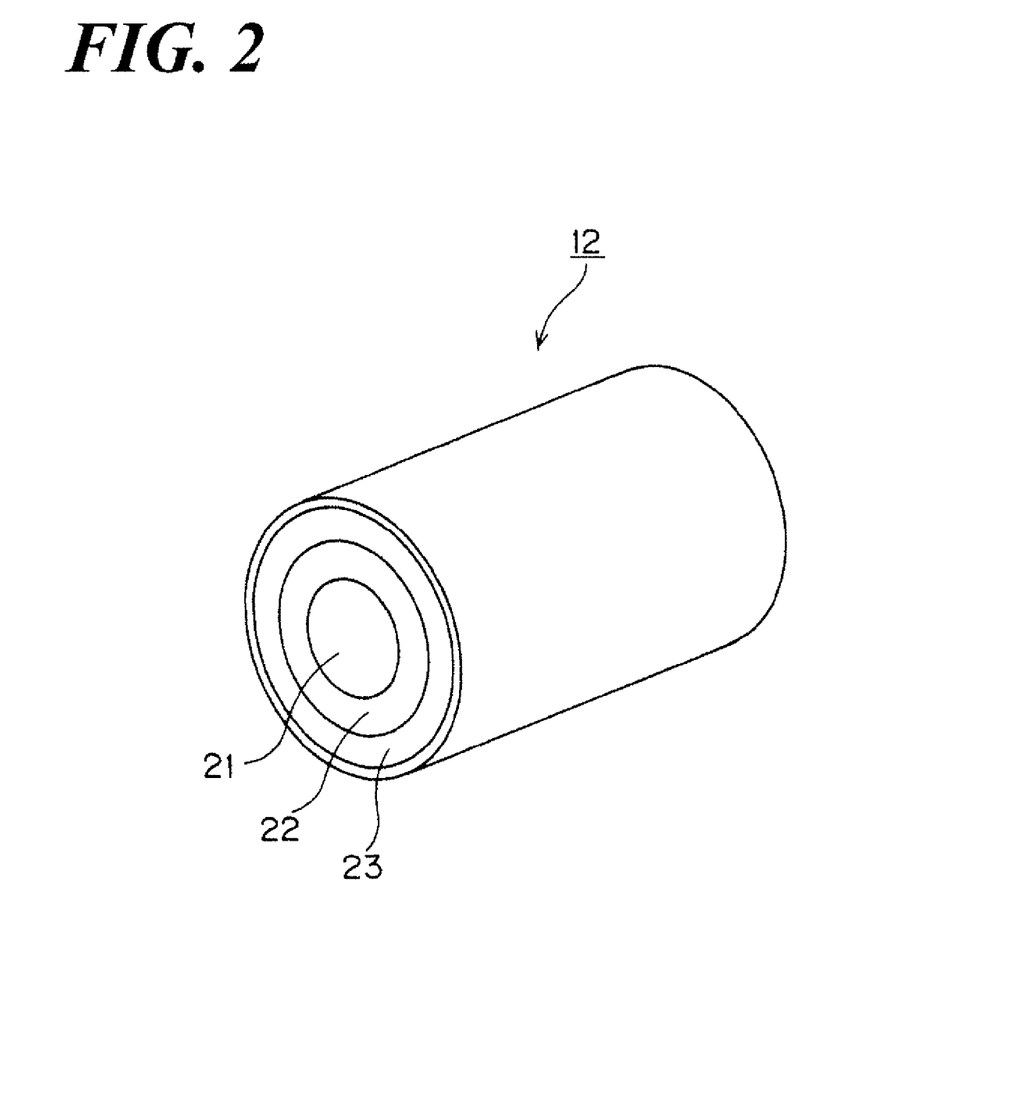
FIG. 2 is a perspective view of a lighting-imaging element 12.

FIG. 2 is the perspective view of a lighting-imaging element 12.

The lighting-imaging element 12 comprises: a camera 21 that can detect near-infrared light and visible light; a visible light source 22 consisting of many LEDs that are mounted to the circumference of the camera 21; an excitation light source 23 consisting of many LEDs that are mounted to the circumference of the visible light source 22. The visible light source 22 irradiates visible light. The excitation light source 23 irradiates near-infrared light having the wavelength 760 nm, which is an excitation light to excite indocyanine green.

Figure 3:
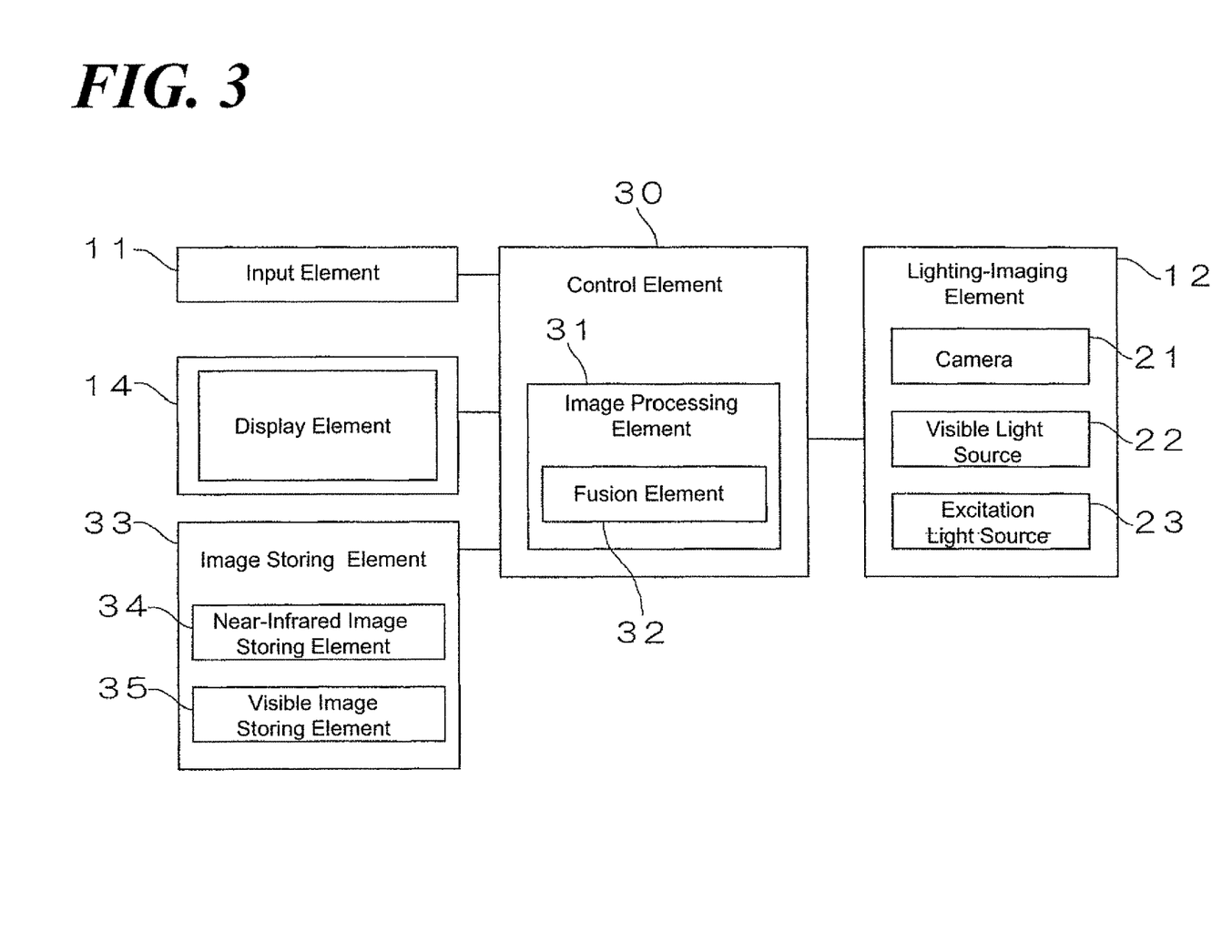
FIG. 3 is a black diagram illustrating the main control system of the imaging device of the present invention.

FIG. 3 is the block diagram illustrating the main control system of the imaging device according to the aspect of the present invention.

Such imaging device comprises: a CPU that executes the logic operation; a ROM that stores operation programs required to control the apparatus; a RAM that stores temporally the data and so forth when controlling; and so forth; and further comprises: a control element 30 that controls the entire apparatus. The control element 30 comprises an image processing element 31 that executes various kinds of imaging processing set forth later and has a fusion element 32. Further, the control element 30 is also connected to the input element 11 and the display element 14 set forth above. In addition, the control element 30 is connected to the lighting-imaging element 12 comprising the camera 21, the visible light source 22 and the excitation light source 23. Further, the control element 30 is also connected to an image storing element 33 that stores images imaged by the camera 21. The image storing element 33 comprises a near-infrared light image storing element 34 that stores the near-infrared image and a visible image storing element 35 that stores the visible images. Meantime, instead of comprising the near-infrared light image storing element 34 and the visible image storing element 35, a fused image storing element that stores the fused images combining the visible image and the near-infrared image can be equipped.

Hereafter, the inventors set forth an operation when a surgical operation is performed by using the imaging device according to the aspect of the present invention. In addition, as set forth below, the case is set forth when the surgery is performed on the breast cancer of a patient 17.

When the breast cancer surgery is performed using such imaging device according to the present invention, indocyanine green is injected to the breast of the patient 17 lying on the treatment table 16. And the near-infrared light is irradiated to the subject including the affected area from the excitation light source 23 and further the visible light is irradiated to the same from the visible light source 22. In addition, the near-infrared light irradiated from the excitation light source 23 is the near-infrared light having the wavelength 760 nm workable as the excitation light for indocyanine green to emit fluorescence. Accordingly, indocyanine green emits the fluorescence in the near-infrared area of which the peak of the wavelength is at approximately 810 nm.

Then the affected area of the patient 17 and the surrounding thereof are imaged by the camera 21. The camera 21 can detect both near-infrared light and visible light. Visible light is irradiated to the patient 17 and the image taken by the camera 21 is the visible image, and near-infrared light is irradiated to the patient 17 and the image obtained by imaging fluorescences emitted from indocyanine green with the camera 21 is the near-infrared image. Referring to FIG. 3, the near-infrared image and the visible image imaged by the camera 21 are forwarded to the imaging processing element 31. The image processing element 31 converts the near-infrared image and the visible image to the displayable image data on the display 14. The near-infrared image data are stored in the near-infrared image storing element 34 of the image storing element 33. The visible image data are stored in the visible image storing element 35 of the image storing element 33.

Under such condition, an image fusion element 32 of the image processing element 31 generates a fused image combining the visible image and the near-infrared image, as set forth later. And the image processing element 31 displays either simultaneously or selectively the near-infrared image, the visible image and the fused image on the display 14, while separating area.

Figure 4:
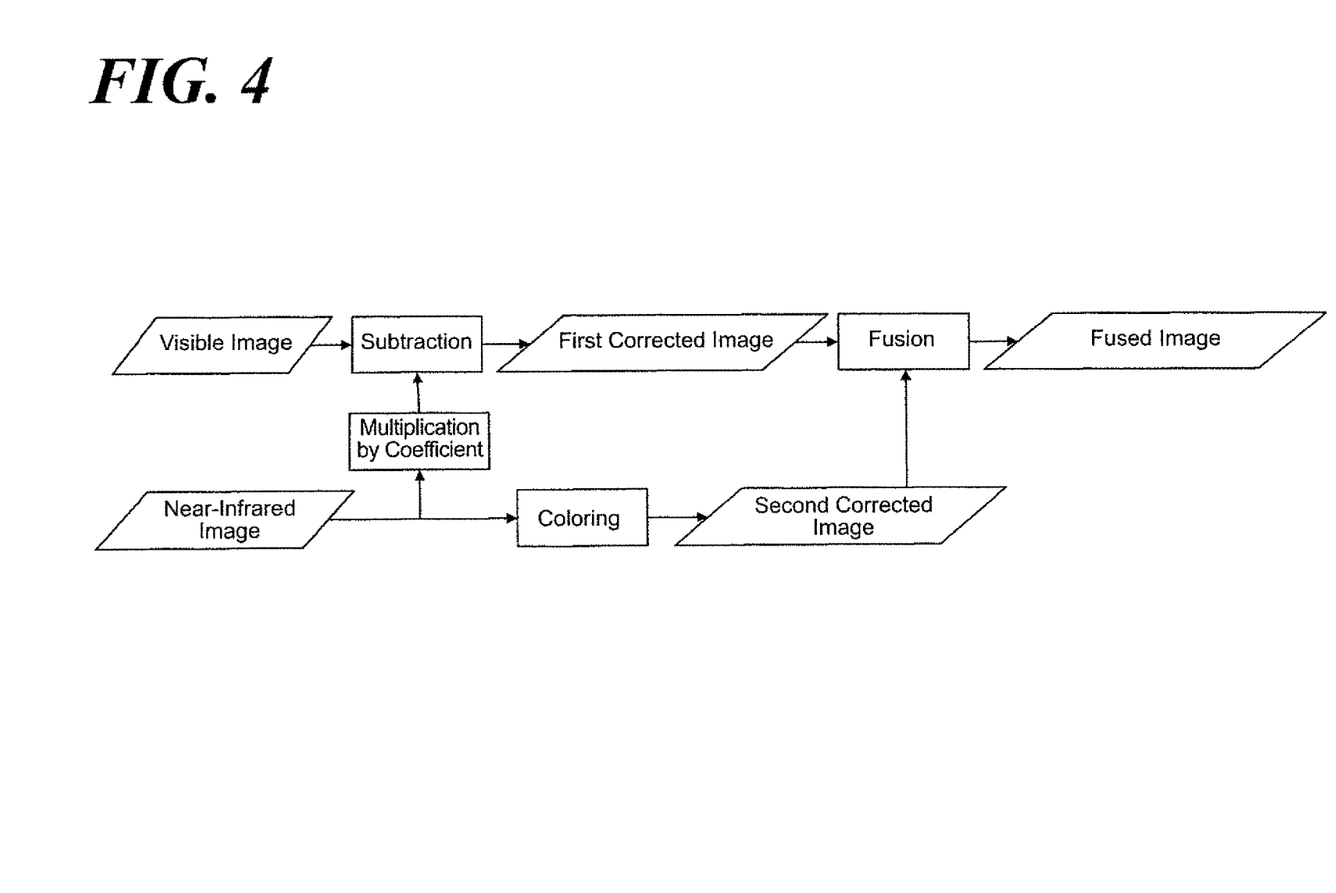
FIG. 4 is a flow-chart illustrating a step of an image fusion process to form a fused image obtained by combing a visible image and a near-infrared image according to the imaging device of the present invention.

Next, the inventor sets forth the generation operation for a fused image characterizing the present invention. FIG. 4 is a flow-chart illustrating a step of an image fusion process to form a fused image obtained by combing a visible image and a near-infrared image according to the imaging device of the present invention.

The fusion element 32 of the imaging processing element 31 generates the fused image by combining: the corrected image generated by using; at least one parameter relative to the color space including RGB value, luminance, value, saturation and hue of each pixel of the visible image, and each pixel value of the near-infrared image imaging fluorescences from indocyanine green; and the second corrected image which is the near-infrared image after colored. Hereafter, the inventors set fort the Embodiment in which a fused image is generated by using three parameters R, G and B of the RGB color space.

It is given that P10i is a pixel value of each pixel of the visible image (i.e., at least one parameter relative to the color space including RGB value, luminance, value, saturation and hue of each pixel of the visible image), and that P20v is a pixel value of each pixel of the near-infrared image. In addition, it is given that P11i is a pixel value of the first corrected image after a subtraction processing set forth later, and that P21i is a pixel value of the second corrected image obtained by coloring the near-infrared image. Further, it is given that P30i is a pixel value of the fused image generated by combining a visible image and a near-infrared image. Here, i is any RGB and v is a integer of from 0 to 255.

The pixel value P11i of each pixel of the first corrected image can be obtained by subtracting the pixel value calculated by multiplying the pixel value of the near-infrared image by a coefficient α selected from a group consisting of natural numbers less than 1 from the pixel value P10i of the visible image, as represented by the following formula. Here, α is the coefficient which is larger than 0 and smaller than 1. In addition, [ ] is a Gauss symbol.

$$P11i = P10i - [\alpha \times P20v + 0.5] \quad (1)$$

And as represented by the following formula (2), the pixel value of the fused image P30i is calculated by executing a screen fusion by utilizing the pixel value of the first corrected image P11i and the pixel value P21i of the second corrected image, which is the near-infrared image after coloring. In addition, if the visible image as the base includes more red area, the color to be used for coloring the near-infrared image can be e.g., blue which can improve visibility thereof.

$$P30i = (P11i + P21i) - (P11i \times P21i)/255 \quad (2)$$

The base visible image is preprocessed with the near-infrared image by executing such calculation, so that the visible image and the near-infrared image can be combined while keeping the color of the colored near-infrared image. Specifically, the near-infrared image corresponding to the fluorescences is subtracted from the visible image and then, the visible image and the near-infrared image can be combined. Accordingly, visibility of the near-infrared image can be improved.

Figure 5:
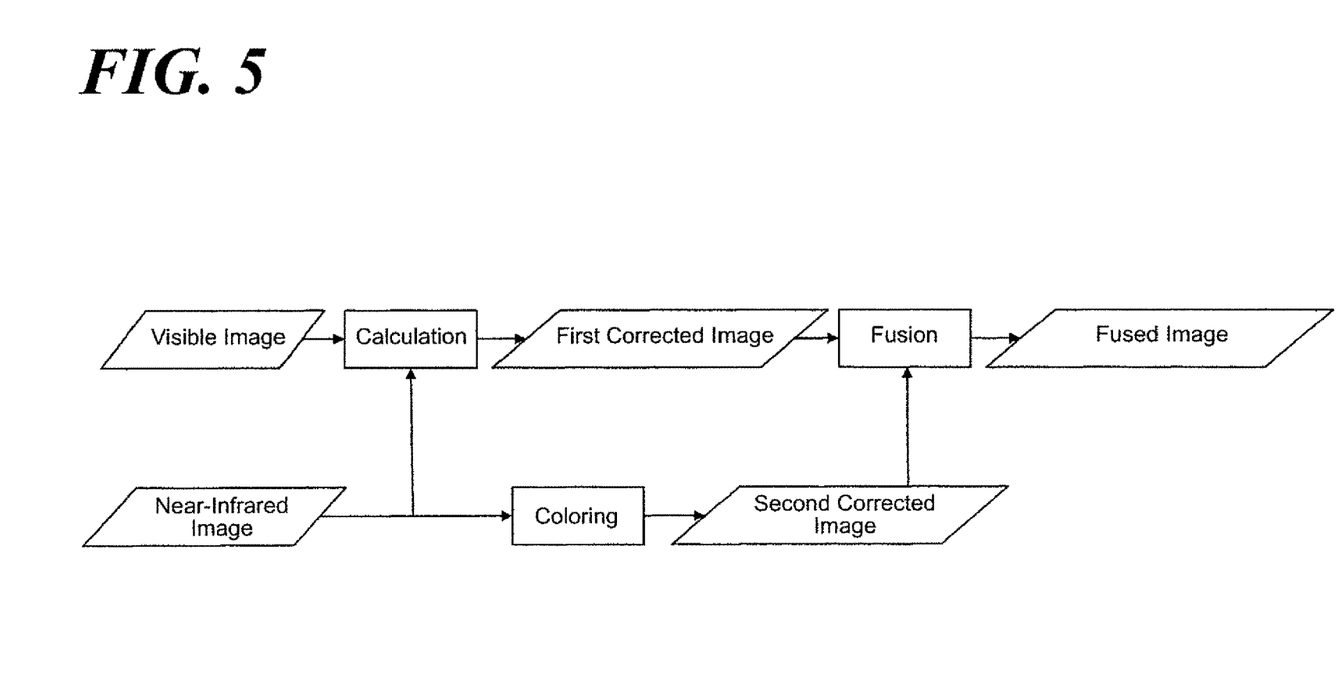
FIG. 5 is a flow-chart illustrating a step of an image fusion process according to the aspect of the other Embodiment to generate a fused image obtained by combing a visible image and a near-infrared image according to the imaging device of the present invention.

Next, the inventors set forth generation operation according to the aspect of the other Embodiment of the fused image, which is a characteristic element of the present invention. FIG. 5 is a flow-chart illustrating a step of an image fusion process of the other Embodiment to generate a fused image obtained by combing a visible image and a near-infrared image according to the imaging device of the present invention.

According to the Embodiment set forth above, the pixel value P11i of each pixel of the first corrected image can be obtained by subtracting the pixel value calculated by multiplying the pixel value of the near-infrared image by a coefficient α, which is a natural number less than 1, from the pixel value P10i of the visible image. On the other hand, according to the aspect of the present Embodiment, the pixel value P11i of each pixel of the first corrected image is calculated based on the following formula (3). In addition, other steps other than the step of generating the first corrected image are the same as the aspect of the Embodiment 1.

$$P11i = 255 - [255 \times (255 - P10i)/(255 - P20v + 1)] \quad (3)$$

Even when such aspect of the Embodiment is applied, the near-infrared image corresponding to the fluorescences is subtracted from the visible image and then, the visible image and the near-infrared image can be combined, so that visibility of the near-infrared image can be improved.

In addition, even according to the aspect of any Embodiments set forth above, the first corrected image is generated using RGB color space as parameters, but instead, the first corrected image can be generated using at least one parameter selected from a group consisting of hue, saturation and value used in the HSV color space or hue, saturation and luminance used in the HLS color space and so forth in such other color spaces.

In addition, according to the aspect of the Embodiment set forth above, the fused image is generated by executing the screen fusion of the first corrected image and the second corrected image, but instead of the screen fusion, other combining methods including an addition fusion and so forth can be applied.

In addition, according to the aspect of the Embodiments set forth above, the near-infrared light having the wavelength 760 nm is applied as the excitation light source 23, but also near-infrared light having any wavelength between approximately 750 nm and approximately 810 nm as the excitation light source 23 can be applied as far as indocyanine green could be excited.

In addition, according to any aspect of the above Embodiments, the inventors set forth the case in which indocyanine green is applied as a material containing a fluorophore and the fluorescence of the near-infrared area having the peak of the wavelength at approximately 810 nm is emitted from indocyanine green by irradiating the near-infrared light having the wavelength 760 nm to such indocyanine green as an excitation light, but a light other than near-infrared light can be applied.

For example, 5-ALA (standing for 5-Aminolevulinic Acid) can be applied as a fluorophore. When 5-ALA is applied, the 5-ALA administered inside the patient's body 17 changes to protoporphyrin IX/PpIX which is a fluorescent substance. When visible light having the wavelength approximately 400 nm is irradiated toward protoporphyrin, red visible light as a fluorescence is emitted from protoporphyrin. Accordingly, when 5-ALA is applied, an excitation light source that irradiates visible light having the wavelength approximately 400 nm can be used.

REFERENCE OF SIGN

10 Main body
11 Input element
12 Lighting-imaging element
13 Arm
14 Display element
16 Treatment table
17 Subject
21 Camera
22 Visible light source
23 Excitation light source
30 Control element
31 Image processing element
32 Fusion element
33 Image storing element
34 Near-Infrared image storing element
35 Visible light image storing element*

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An imaging device, comprising:
an excitation light source that irradiates an excitation light to a subject;
   wherein the excitation light excites a fluorophore administered into said subject to produce a fluorescence;
a visible light source that irradiates a visible light to said subject;
a camera capable of detecting the fluorescence and the visible light;
   wherein said fluorescence is emitted from said fluorophore due to said irradiation of the excitation light and said visible light is reflected from a surface of said subject; and
an image fusion element that generates a fused image by combining a visible image of the subject and a fluorescent image of the subject imaged by the camera; and
wherein said image fusion element generates a first corrected image by modifying a pixel value of an area of said fluorescent image relative to said visible image using said visible image and said fluorescent image, generates a second corrected image by coloring said fluorescent image and combining said first corrected image and said second corrected image.

2. The imaging device according to claim 1, wherein:
said image fusion element that generates said fused image by combining the first corrected image further obtains said first corrected image by subtracting an image based on said fluorescent image from said visible image and the second corrected image obtained by coloring said fluorescent image.

3. The imaging device according to claim 2, wherein:
said first corrected image is generated by subtracting the pixel value, which is obtained by multiplying a pixel value of said fluorescent image by a coefficient from a value of a color space of said visible image, and the coefficient is larger than 0 and smaller than 1.

4. The imaging device according to claim 2, wherein:
said excitation light and said fluorescence are near-infrared lights.

* * * * *